United States Patent [19]

Los

[11] 4,273,777
[45] Jun. 16, 1981

[54] METHODS OF TREATING MAMMALS SUFFERING FROM INFLAMMATION AND PAIN

[75] Inventor: Mario A. Los, Capital Federal, Argentina

[73] Assignee: Laboratorios Bago S.A., Argentina

[21] Appl. No.: 149,435

[22] Filed: May 13, 1980

Related U.S. Application Data

[60] Division of Ser. No. 44,944, Jun. 4, 1979, which is a continuation-in-part of Ser. No. 2,225, Jan. 9, 1979, abandoned.

[51] Int. Cl.³ ............................................. A61K 31/44
[52] U.S. Cl. .................................................... 424/263
[58] Field of Search ........................................ 424/263

Primary Examiner—Stanley J. Friedman
Attorney, Agent, or Firm—Kane, Dalsimer, Kane, Sullivan and Kurucz

[57] ABSTRACT

The disclosure is of a class of organic compounds and pharmaceutical compositions containing them as the active ingredient thereof, which are useful for the alleviation of pain and/or inflammation in mammals, including humans, suffering from pain and/or inflammation.

4 Claims, No Drawings

METHODS OF TREATING MAMMALS SUFFERING FROM INFLAMMATION AND PAIN

CROSS-REFERENCE TO RELATED APPLICATION

This is a division of application Ser. No. 44,944, filed June 4, 1979, which is a continuation-in-part of my copending U.S. patent application Ser. No. 2,225 filed on Jan. 9, 1979, now abandoned.

BACKGROUND OF THE INVENTION

1. Field of the Invention

The invention relates to methods and pharmaceutical preparations for the alleviation of pain and/or inflammation in mammals, including humans, suffering from pain and/or inflammation.

2. Brief Description of the Prior Art

The prior art literature is replete with disclosures of the synthesis and therapeutic properties of a large number of organic acid compounds useful as analgesics and as anti-inflammatory agents. For example, o-acetylsalicylic (U.S. Pat. Nos. 2,731,492; 2,890,240; 3,235,583) and 2-(3'-chloro-2'-methylanilino)pyridine-3-carboxylic acids (British Pat. No. 1,147,702) are known to have an analgesic effect. [3'-(trifluoromethyl)phenyl]anthranylic (Wilkinson, Finar J. Chem. Soc. 32, 1948), N-(2',3'-xylyl)anthranylic (Belgium Pat. No. 605,302) and 2(3'-trifluoromethyl)anilino)pyridine-3-carboxylic acids (Netherland Pat. No. 6,414,717) are known to have an anti-inflammatory effect when administered to mammals. However, these anti-inflammatory and analgesic phenyl- and pyridine-3-carboxylic acids are also known to have an ulcerogenic side-effect. In hope of reducing this side-effect, different derivatives of the above-described compounds were synthesized. Thus, aminoalkyl esters of 2-anilino nicotinic acids are described in French Pat. No. 2,187,317; glyceryl esters of 2-anilino-nicotinic acids are disclosed in Swiss Pat. No. 534,130 and South African Pat. No. 6,802,185. Also, different esters of N-phenyl-anthranylic acids were prepared as were aminoalkyl esters (Belgian Pat. Nos. 612,424 and 630,053), ethyl and methyl esters (French Pat. M No. 2948), methyl ester (Japanese Pat. No. 75 11.904) and glyceryl esters (U.S. Pat. No. 3,852,333 and South African Pat. No. 70-07385) in hopes of finding related anti-inflammatory and analgesic compounds free of the ulcerogenic side-effects. So also, various salts of phenyl and pyridine-3-carboxylic acids were synthesized and evaluated. For example, arginine, lysine, choline and aluminum salts are described in Japanese Pat. Nos. 71-29,735; 72-21,597 and 74-125,512; German Pat. Nos. 2,253,134 and 2,442,817; and Argentinian Pat. No. 197,737. However, the search for analgesic and anti-inflammatory compounds free of ulcerogenic activity has not heretofore been completely successful.

We have now found a class of compounds which have analgesic and anti-inflammatory activity without the characteristic ulcerogenic side-effects mentioned above. This side-effect (described in the literature; see Sherrer and Whitehouse, Anti-inflammatory Agents, Chemistry and Pharmacology, 13-1, Academic Press, New York 1974) has an ulcerogenic effect on the gastric epithelium. The esters of pyridine-3-carboxylic acids of general formula (I) infra., were tested on mammals and the test results showed an increased anti-inflammatory activity (possibly due to an enhanced gastrointestinal absorption) and non-ulcerogenic effects. It is believed that the compounds of general formula (I) are absorbed through gastrointestinal epithelium where they are hydrolyzed by enzymes in the recipient mammal's blood, to corresponding pharmacologically active acids.

SUMMARY OF THE INVENTION

The invention comprises a method of alleviating pain and inflammation in mammals, including humans, suffering from pain and inflammation, which comprises; administering to the mammal an effective amount of a compound selected from those of the formula:

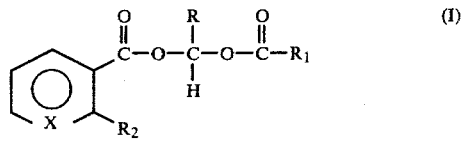

wherein X represents a moiety of formula:

$-N=$;

R taken independently is hydrogen; $R_1$ taken independently is isobutyl; and R and $R_1$ when taken together form the divalent moiety of formula:

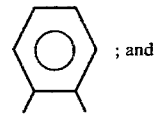 ; and $R_2$ is a group of formula:

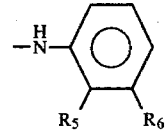

wherein when $R_1$ and R are taken together, then $R_5$ is methyl and $R_6$ is chlorine, and when $R_1$ is isobutyl and R is hydrogen, then, $R_5$ is selected from the group consisting of hydrogen and methyl and $R_6$ is selected from the group consisting of chlorine and trifluoromethyl; and the pharmaceutically acceptable acid addition salts thereof.

The invention also comprises pharmaceutical compositions for treating pain and inflammation in a mammal, which comprises; an effective amount of the above-described compounds of formula (I) in admixture with a pharmaceutical carrier.

The method and compositions of the invention are useful for alleviating inflammation and pain associated with inflammation in mammals, including humans, with minimum potential for ulcerogenic side-effects. More specifically, the method and compositions of the invention are useful for the treatment of inflammation and pain associated with a variety of clinical conditions such as rheumatoid arthritis, osteoarthritis, phlebitis, rheumatoid fever fibrositis, tendinitis, bursitis, inflammation and pain provoked by infectious disease (in conjunction with appropriate treatment of the infection) and like clinical conditions.

DETAILED DESCRIPTION OF THE PREFERRED EMBODIMENTS OF THE INVENTION

Compounds of the formula (I) given above were heretofore known. Representative of such compounds are the phthalidylic ester of 2-(3'-chloro-2-methylanilino)pyridine-3-carboxylic acid; pivaloyloxymethyl esters of 2-(3'-(trifluoromethyl)anilino)pyridine-3-carboxylic and 2-(3'-chloro-2'-methyl-anilino)pyridine-3-carboxylic acids and the like. Methods for the preparation of the compounds of formula (I) are also known. One such process comprises the reaction between a previously salified pyridine-3-carboxylic acid of formula II and a compound of formula (III), infra.

The synthesis' scheme is illustrated by the formulae:

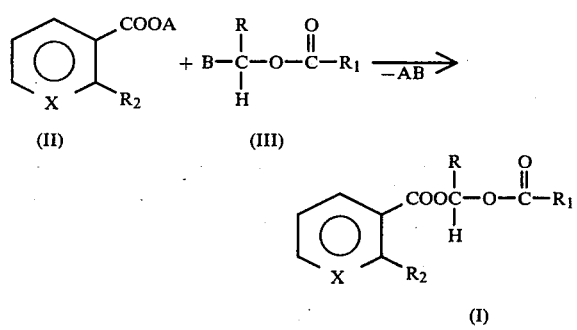

wherein X, R, $R_1$ and $R_2$ are as previously defined; A can be a hydrogen atom or a base, and B can be hydroxyl or halogen.

The preparation of salified pyridine-3-carboxylic acids of formula II is likewise well known. More specifically the salification of pyridine-3-carboxylic acids may be performed with an inorganic or organic base of formula:

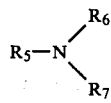

wherein $R_5$, $R_6$ and $R_7$ independently are selected from hydrogen, aryl, alkyl or aliphatic alcohol radicals, such as: diethylamine, diethanolamine, benzylamine, cyclohexylamine, and the like. Triethylamine is the organic base preferentially used. The molar ratio of the reactants may be in a range of 1.3–2 moles of base for each mole of acid, and the reaction is preferably carried out in polar solvents such as acetone, dimethylacetamide, dimethylformamide and the like at a temperature of 20°–25° C.

After the salification of the acid, the product salt is then reacted with the compound of formula (III) in a ratio of 1–1.5 moles of the compound (III) for each mole of acid of formula (II) to obtain compounds of the general formula (I). For example, using 3-bromophthalide as the compound (III), phthalydil esters are prepared. 3-bromophthalide is a known compound synthesized by bromination of phthalide with N-bromosuccinimide in the presence of a catalyst and anhydrous carbon tetrachloride (Org. Synth. 42, 26, 1962) or by adding gaseous bromide into a previously melted phthalide at a temperature of 140°–155° C. (Org. Synth., Coll. Vol. 3, 737, 1955).

The reaction between salts of pyridine-3-carboxylic acid and pivaloyloxymethyl chloride gives the corresponding pivaloyloxymethyl esters. The preparation of this halogenated derivative is performed through the reaction of equimolar amounts of paraformaldehyde and pivaloyl chloride in the presence of a catalyst such as zinc chloride (Rasmussen and Leonard, J. Am. Chem. Soc. 89, 5442, 1967).

The reaction between pivaloyloxymethylchloride or 3-bromophthalide and pyridine-3-carboxylic salts is advantageously carried out in a reaction medium which comprises a solvent or mixture of them, in which the reactants and the product compound are perfectly soluble. Further, since the presence of water hydrolyzes 3-bromophthalide to phthalaldehydic acid (Org. Synth. Coll. Vol. 3, 737, 1955) and decomposes pivaloyloxymethyl chloride to the corresponding alkyloxylalcanol, the reaction medium is preferably anhydrous.

The separation of the compounds of formula (I) from the producing reaction mixtures depends on the reaction medium and physico-chemical properties of each compound. For example, phthalydil ester of 2(3'-chloro-2'-methylanilino)-pyridine-3-carboxylic acid and pivaloyloxymethyl esters of 2-(3'-chloro-2-methylanilino)pyridine-3-carboxylic acid may be separated by adding water to the reaction medium when it consists of acetone to precipitate the desired product. The precipitate may be filtered, washed and if desired recrystallized to obtain the desired product in relatively pure forms.

On the other hand, phthalidyl esters of 2-(2'-methyl-3-chloro anilino)-pyridine-3-carboxylic in dimethylformamide, is readily extracted from reaction mediums after water is added, using extractive solvents such as: ethyl, propyl, butyl acetates, dichloromethane and the like.

The compounds (1) may be used in the present invention in either the free acid form or in the form of an acid addition salt. The acid addition salts may be prepared by reacting the free compound (1) with a stoichiometric proportion of an appropriate acid such as hydrochloric acid. The method is well known to those skilled in the art, and may be carried out in aqueous or non-aqueous media such as ethanol, ether, ethyl acetate and the like.

The pharmaceutically acceptable acid addition salts may be used for the same purposes as the free acid. Illustrative of pharmaceutically acceptable acid addition salts are those formed upon reaction of the compounds (1) with hydrochloric acid, hydrobromic acid, sulfuric acid, phosphoric acid, acetic acid, lactic acid, citric acid, succinic acid, benzoic acid, salicylic acid, pamoic acid, cyclohexanesulfamic acid and the like.

This invention relates also to pharmaceutical dosage unit forms for systemic administration (oral, topical and parenteral administration) which are useful in treating inflammation and pain in mammals, including humans. The term "dosage unit form" as used in this specification and in the claims refers to physically discrete units suitable as unitary dosage for mammalian subjects, each unit containing a predetermined quantity of the essential active ingredient, i.e.; a compound (1) or a pharmaceutically acceptable acid addition salt thereof, calculated to produce the desired effect in combination with the required pharmaceutical means which adapt said ingredient for systemic administration. Examples of dosage unit forms in accordance with this invention are tablets, capsules, orally administered liquid preparations in liquid vehicles, sterile preparations in liquid vehicles, sterile preparations in liquid vehicles for intramuscular and intravenous administration, suppositories, and sterile dry preparations for the extemporaneous preparation of sterile injectable preparations in a liquid vehicle. Solid diluents or carriers for the solid oral pharmaceutical dosage unit forms are selected from the group consisting of lipids, carbohydrates, proteins and mineral solids, for example, starch, sucrose, kaolin, dicalcium phosphate, gelatin, acacia, corn syrup, corn starch, talc and the like. Capsules, both hard and soft, are formulated with conventional diluents and excipients, for example, edible oils, talc, calcium carbonate, calcium stearate, magnesium stearate and the like. Liquid pharmaceutical preparations for oral administration may be prepared in water or aqueous solutions which advantageously contain suspending agents, such as for example, sodium carboxymethylcellulose, methylcellulose, acacia, polyvinyl pyrrolidone, polyvinyl alcohol and the like. In the instance of injectable forms, they must be sterile and must be fluid to the extent that easy syringeability exists. Such preparations must be stable under the conditions of manufacture and storage, and ordinarily contain in addition to the basic solvent or suspending liquid, preservatives in the nature of bactericidal and fungicidal agents, for example, parabens, chlorobutanol, benzyl alcohol, phenol, thimerosal, and the like. In many cases it is preferable to include isotonic agents, for example, sugars or sodium chloride. Carriers and vehicles include vegetable oils, water, ethanol, and polyols, for example, glycerol, propylene glycol, liquid polyethylene glycol, and the like. Any solid preparations for subsequent extemporaneous preparation of sterile injectable preparations are sterilized, preferably by exposure to a sterilizing gas, such as for example, ethylene oxide. The aforesaid carriers, vehicles, diluents, excipients, preservatives, isotonic agents and the like constitute the pharmaceutical means which adapt the preparations for systemic administration.

The pharmaceutical dosage unit forms are prepared in accordance with the preceding general description to provide an effective amount of the essential active ingredient (a compound of formula (I)) per dosage unit form in admixture with the means for adaptation to systemic administration. In general, the unit dose form will contain 3 to 73 percent by weight of the essential active ingredient.

It will be appreciated that the exact dosage of a compound of the formula (I) constituting an effective amount for treatment of a mammal according to the method of the invention will vary greatly depending on the specific nature of the clinical condition being treated, severity of the condition, species of mammal; age, weight and condition of the mammal, mode of administration of the dosage form and the specific compound of formula (I) being administered. The exact dose required for a given situation may be determined by administration of a trial dose and observation of the clinical response. In general, an effective amount to be administered will be within a range of from about 0.1 mg per kg. to about 50 mg. per kg. of body weight of the recipient, daily. Preferably 0.5 mg./kg. to about 25 mg./kg. daily is provided. In most instances, a single administration will effect the desired response and bring about the result desired. In cases such as the treatment of epidermal conditions however, it may be desirable to repeat the administrations several times.

The following examples and preparations describe the manner and process of making and using the invention and set forth the best mode contemplated by the inventor of carrying out the invention but are not to be construed as limiting.

Preparation I

Phthalydil 2(3'-chloro-2'-methylanilino)pyridine 3-carboxylate 2-(3'-Chloro-2'-methylanilino)pyridine-3-carboxylic acid (39.4 g) was suspended in 520 ml of acetone, and then triethylamine (28 ml) was added. After stirring for 20 minutes to obtain a solution, 3-bromophthalide (42.6 g) was poured into the solution. After the addition, the mixture was refluxed 6 hours and then cooled to ambient temperature. With continuous stirring, the reaction mixture was poured into 2000 ml of distilled water, and then cooled to 5° C., maintaining that temperature for 3 hours. The precipitate was collected by filtration, and dried at 40° C. under vacuum to obtain 53 g (89.7% of theory) of crude phthalydil 2(3'-chloro-2'-methyl anilino)pyridine-3-carboxylate (m.p. 179°–181° C.).

Recrystallization from isobutyl acetate gives 43.8 g (74.1% of theory) of the purified compound (m.p. 182°–184° C.).

Preparation II

Phthalydil 2-(2'-methyl-3'-chloroanilino)-pyridine-3-carboxylate

2(2'-methyl-3-chloroanilino)pyridine-3-carboxylic acid (65.7 g) was suspended in 250 ml of dimethylformamide and then triethylamine (52.5 ml) was added. After the addition, the reaction mixture was stirred for 30 minutes, then 3-bromophthalide (53.3 g) was added. The reaction mixture was warmed gently to 30° C. ±2 and maintained at this temperature for 6 hours. Then 850 ml of isobutyl acetate was added, and the mixture filtered. The filtrate was extracted with 200 ml portions of distilled water 4 times. The phase layers were separated and the aqueous layer discarded. The organic extract was dried over anhydrous sodium sulfate and after filtration it was concentrated to ¼ of its initial volume, under vacuum at a temperature of 30°–35° C. The concentrate was cooled in an ice/water bath until a compound was completely crystallized. The precipitate was filtered by suction and washed with previously cooled isobutyl acetate, and then dried under vacuum to obtain a yield of 64.7% (64.1 g) of phthalydil ester of 2(3'-chloro-2'-methylanilino)-pyridine-3-carboxylic acid (m.p. 183°–184° C.).

Preparation III

Pivaloyloxymethyl 2-(3'-chloro-2'-methylanilino)-pyridine-3-carboxylate

To a stirred mixture of 2-(3'-chloro-2'-methylanilino)-pyridine-3-carboxylic acid (26.3 g) in 400 ml of acetone, triethylamine (20.5 ml) was added. Thereafter pivaloyloxymethyl chloride (15 ml) was poured into the mixture and then it was refluxed 4 hours. Subsequently, the reaction mixture was cooled to 15°–20° C. poured into previously cooled distilled water (3000 ml) and maintained at 5°–7° C. for 4 hours. The cake was filtered by suction and the formed compound dried at 25°–35° C. under vacuum to obtain a yield of 77.4% (29.2 g) of pivaloyloxymethyl 2-(3'-chloro-2'-methylanilino)-pyridine-3-carboxylate, m.p.: 91° C.–92° C.

Preparation IV

Pivaloyloxymethyl 2-(3'-trifluoromethylanilino)-pyridine-3-carboxylate

To 2-(3'-trifluoromethyl-anilino)-pyridine-3-carboxylic acid (39.5 g) in 400 ml acetone, triethylamine (29 ml) and pivaloyloxymethyl chloride (21 ml) were added with continuous stirring (over 1 hour). The mixture was refluxed 4 hours, and then cooled to 25°–25° C. To the mixture there was added 3000 ml of distilled water. The resulting mixture was extracted twice with 60 ml portions of dichloromethane. The separated organic layer was dried over anhydrous magnesium sulfate, then concentrated to 1/6 of its initial volume under vacuum at 39°–46° C. To the concentrate 100 ml of petroleum ether was added. The formed precipitate was filtered by suction and dried under vacuum at 25°–35° C.

Yield: 85.2% (47.4 g) of pivaloyloxymethyl 2-(3'-trifluoromethylanilino)-pyridine-3-carboxylate, m.p.: 55°–56° C.

EXAMPLE 1

Three thousand tablets for oral use, each containing 500 mg of essential active ingredient (e.g. an amount of phthalidyl-2-(3'-chloro-2'-methylanilino)pyridine-3-carboxylate (Preparation 1, supra.) equivalent in anti-inflammatory and analgesic activity to 500 mg of 2-(3'-chloro-2'-methylanilino)pyridine-3-carboxylate acid), were prepared from the following ingredients:
- essential active ingredient: 1500 g
- starch (Rx-1500): 300 g
- magnesium stearate, USP: 39 g
- colloidal silicic acid: 19.5 g
- Avicel ® pH 102, q.s. to: 3900 g The essential active ingredient was ground through a 0.25 mm sieve opening screen. The powdered active ingredient, with 50% of the total amount of magnesium stearate to be used, colloidal silicic acid and Avicel ® pH 102 were passed through a 40 mesh sieve, mixed for 20 minutes and then slugged. The slugs were broken down by forcing through a screen No. 11, and mixed with the remaining magnesium stearate and compressed into tablets.

One tablet given orally 1 or 2 times a day is useful in the relief of nociceptive effect and inflammation in adult humans provoked by infective disease, or other etiological causes.

EXAMPLE 2

Three thousand capsules for oral use, each containing 250 mg of phthalydil-2(3'-chloro-2'-methylanilino)pyridine-3-carboxylate as the essential active ingredient, were prepared from the following ingredients:
- essential active ingredient: 750 g
- colloidal silicic acid: 30 g
- magnesium stearate USP: 30 g
- microcrystalline cellulose: 150 g
- lactose: 90 g In accordance with the active ingredient potency, the amount of lactose was adjusted to achieve a weight of 900 mg for each capsule. The ingredients were passed through a 40 mesh sieve and mixed for 30 minutes. Hard gelatin capsules No. 0 were filled using Zanazi, model RV-59 equipment. The capsules were preserved in airtight, light-resistant containers.

This combination of active materials is effective in reducing inflammation and pain in humans. The dose is one to three capsules administered orally, depending on the severity of the condition.

EXAMPLE 3

An ointment containing 3% of essential active ingredient (e.g. an amount of pivaloyloxymethyl 2-(3'-trifluoromethylanilino)pyridine-3-carboxylate equivalent to 3% of 2-(3'-trifluoromethylanilino)pyridine-3-carboxylic acid) was prepared from the following ingredients:
- essential active ingredient: 300 g
- cetyl alcohol: 450 g
- stearyl alcohol: 450 g
- polysorbate 60: 440 g
- liquid petrolatum: 400 g
- isopropyl miristate: 200 g
- sorbitol solution, USP: 600 g
- Span ® 80: 60 g
- methylparaben: 18 g
- propylparaben: 5 g
- purified water q.s. to: 10,000 g Cetyl alcohol, stearyl alcohol, Span ® 80, isopropyl miristate and liquid petrolatum were melted into a heating mixer, and 50% of the total amount of methyl paraben and isopropylparaben were added. The mixture was maintained at 60°–70° C. Purified water was poured into another heating mixer, and heated to 80° C. The remaining methylparaben and propylparaben were added and dissolved. Polysorbate 60 and sorbitol solution were poured into the heated water and the temperature was maintained at 60°–70° C. Then, the aqueous solution was mixed with the first preparation, forming an oil in water emulsion. When the temperature diminished to 40°–45° C., the powdered essential active ingredient was added, maintaining the stirring until the mixture reached room temperature.

This ointment is useful in the treatment of humans for local pain or inflammation and may be topically applied three times a day on the affected area.

EXAMPLE 4

One thousand suppositories each weighing 3 g and containing 500 mg of essential active ingredient, were prepared from the following ingredients:
- essential active ingredient (phthalydil-2(3'-chloro-2'-methylanilino)pyridine-3-carboxylate: 500 g
- natural hydrogenated glycerides: 3,000 g The powdered essential active ingredient is added to the previously melted natural hydrogenated glycerides. The mixture is stirred and maintained at 45°–50° C. for 30 minutes. The suspension is poured into molds and allowed to cool and solidify.

These suppositories are useful in the treatment of pain and inflammation in mammals, when administered at a dose of 1 suppository administered rectally twice a day.

EXAMPLE 5

Following the procedure of the preceding Examples 1 to 4, inclusive, dosage forms of the invention are prepared by using an equivalent amount of different compounds of the formula (I) such as for example, phthalidyl and pivaloyloxymethyl 2-(3'-chloro-2'-methyl anilino)-3-pyridine carboxylate, pivaloyloxymethyl 2-(3'-trifluoromethylanilino)-3-pyridine carboxylate and the like.

In the following examples, the compounds of the formula (I) were subjected to comparative pharmacological tests to determine their therapeutic effects.

EXAMPLE 6

Anti-inflammatory Activity (Carrageenin induced edema test)

The method of Winter, Risley and Nuss (Winter, C. A., Risley, E. A. and Nuss G. W., Proc. Soc. Exp. Biol. Med. 111, 544, 1962) was used. Fifteen to twenty male rats of Sprague Dawley strain weighing 150–200 g, were employed for each compound tested. 0.1 ml of 1% carrageenin saline suspension was injected into the subplantar region of the right hind-paw. The test compounds were orally administered 30 minutes prior to the injection of carrageenin and the foot volume was determined 1, 3 and 5 hours after the injection of carrageenin. The percent swelling in the foot was obtained by comparing the volume before and after the injection of carrageenin, and the rate of inhibition in the treated animals was calculated. The results are shown in the following table:

| Compound Tested | Dose mg/kg Weight | % Edema Inhibition | | |
|---|---|---|---|---|
| | | 1 hour | 3 hours | 5 hours |
| Acetylsalicylic acid (ASA) | 100 | 3.8 | 24.8 | 25.3 |
| 2-(3'-trifluoromethyl-anilino)-3-pyridinecarboxylic acid (TPA) | 47 | 32.0 | 42.8 | 44.0 |
| Pivaloyloxymethyl 2-(3'-trifluoromethyl-anilino)-3-pyridinecarboxylate | 66 ② | 69.4 | 54.3 | 47.2 |
| 2-(3'-chloro-2'-methyl-anilino)-3-pyridinecarboxylic acid (CPA) | 150 | 17.8 | 21.4 | 17.4 |
| Phthalidyl 2-(3'-chloro-2'-methyl-anilino)-3-pyridine carboxylate | 216 ③ | 21.1 | 23.7 | 29.4 |
| Pivaloyloxymethyl 2-(3'-chloro-2'-methylanilino)-3-pyridine carboxylate | 207 ③ | 29.6 | 25.8 | 26.4 |
| Phthalidyl N-(2',3'-xylyl) anthranylate | 186 | 27.4 | 34.2 | 30.4 |
| Pivaloyloxymethyl N-(2',3'-xylyl) anthranylate | 196 | 33.3 | 36.4 | 31.3 |
| N-(3'-trifluorotolyl)-anthranylic acid (TAA) | 60 | 24.3 | 29.3 | 28.3 |
| Phthalidyl N-(3'-trifluorotolyl) anthranylate | 88 | 35.4 | 40.2 | 37.4 |
| Pivaloyloxymethyl N-(3'-trifluorotolyl) anthranylate | 84.5 | 40.4 | 40.7 | 32.4 |

② Equivalent to 47 mg of TPA
③ Equivalent to 100 mg of CPA

EXAMPLE 7

Analgesic Activity

The compounds were tested using a tail pressure test and the Randall Selitto's test (Randall, L. O., Selitto, J. J., Arch. Int. Pharmacodyn. 111, 409, 1957).

Tail pressure test: Ten male mice of Rockland strain weighing 20–25 g were used for each compound tested. The response threshold on applying pressure to the tail was determined with an analgesy meter at 15 and 60 minutes after oral administration of the test compound. The pressure at which a struggle was elicited was read.

Randall-Selitto's method: Ten male mice of Rockland strain weighing 25 g were used for each compound tested. 0.1 ml of 1% carrageenin saline suspension was injected into the subplantar region of the right foot. The test compounds were orally administered 30 minutes before the injection. At hourly intervals for 3 hours after the carrageenin injection, the pain threshold for the inflammed feet was measured determining the amount of pressure with an analgesy meter.

The results of these tests were observed as relative potency, as follows:

| Compound Tested | Dose mg/kg Weight | Relative strength | |
|---|---|---|---|
| | | Tail pressure test | Randall-Selitto test |
| Control (water) | — | 0 | 0 |
| Acetylsalicylic acid (ASA) | 100 | 1.00 | 1.05 |
| Pivaloyloxymethyl 2-(3'-trifluoromethylanilino)-3-pyridinecarboxylate | 166 ① | 1.94 | 1.37 |
| Pivaloyloxymethyl 2-(3'-trifluoromethylanilino) 3-pyridinecarboxylate | 66 ② | −0.3 | 12.3 |
| 2-(3'-chloro-2-methylanilino) 3-pyridinecarboxylic acid (CPA) | 50 | 4.20 | 4.35 |
| 2-(3'-trifluoromethylanilino)-3-pyridinecarboxylic acid (TPA) | 47 | 0 | 8.0 |
| Phthalidyl 2-(3'-chloro-2'-methylanilino)-3-pyridine-carboxylate | 72 ③ | 2.01 | 12.4 |
| Pivaloyloxymethyl 2-(3'-chloro-2'-methylanilino)-3-pyridine carboxylate | 69 ③ | 1.98 | 10.2 |
| Phthalidyl N-(2',3'-xylyl) anthranylate | 77 | 0.56 | 1.37 |
| Pivaloyloxymethyl N-(2',3'-xylyl) anthranylate | 74 | 0.48 | 1.74 |
| N-(3'-trifluorotolyl) anthranylic acid (TAA) | 50 | 0.5 | 5.3 |
| Phthalidyl N-(3'-trifluorotolyl) anthranylate | 73.5 | 0.74 | 10.6 |
| Pivaloyloxymethyl N-(3'-trifluorotolyl) anthranylate | 82 | 1.02 | 8.7 |

① Equivalent to 100 mg of ASA
② Equivalent to 47 mg of TPA
③ Equivalent to 50 mg of CPA

EXAMPLE 8

Influence on the gastro-intestinal tract

Ten male rats of Sprague Dawley strain, weighing 200–300 g were used for each compound tested. According to the method of Shay et al. (Shay, H., Komapov. S. A., Feb. S. S., Meranir, D., Gruenstein, M., Siplet, H. Gastroenterology 5, 43, 1945), under anesthesia, the pylorus was ligated and 4 hours later test compounds were orally administered. The animal was sacrificed 1 hour after compound administration. The stomach was removed and examined for macroscopic damage. The ulceration of the gastric epithelium was evaluated by the following evaluation: 0=no hemorrhage sites; 1=some isolated hemorrhagic sites; 2=redness of the gastric epithelium; 3=1 to 5 small ulcers with a diameter smaller than 3 mm; 4=many small ulcers; 5=ulcers—greater than 3 mm; 6=perforated ulcer.

The results of this test were as follows:

| Compound Tested | Dose mg/kg Weight | Evaluation | Increase |
|---|---|---|---|
| Control (distilled water) | — | 3.0 | — |
| Phenylbutazone | 75 | 5.5 | 2.5 |
| Acetylsalicylic acid | 100 | 4.1 | 1.1 |
| 2-(3'-trifluoromethyl-anilino)-3-pyridinecarboxylic acid | 47 | 3.9 | 0.9 |
| Pivaloyloxymethyl 2-(3'-trifluoromethylanilino)-3-pyridinecarboxylate | 66 | 3.2 | 0.2 |
| 2-(3'-chloro-2'-methylanilino)-3-pyridinecarboxylic acid | 150 | 4.0 | 1.0 |

| Compound Tested | Dose mg/kg Weight | Evaluation | Increase |
|---|---|---|---|
| Phthalidyl 2-(3'-chloro-2'-methylanilino)-3-pyridine-carboxylate | 216 | 3.6 | 0.6 |
| Pivaloyloxymethyl 2-(3'-chloro-2'-methylanilino)-3-pyridine-carboxylate | 207 | 3.0 | — |
| Phthalidyl N-(2',3'-xylyl) anthranylate | 186 | 3.3 | 0.3 |
| Pivaloyloxymethyl N-(2',3'-xylyl) anthranylate | 196 | 3.4 | 0.4 |
| N-(3'-trifluorotolyl)anthranylic acid | 60 | 4.9 | 1.9 |
| Phthalidyl N-(3'-trifluorotolyl) anthranylate | 88 | 3.5 | 0.5 |
| Pivaloyloxymethyl N-(3'-trifluorotolyl) anthranylate | 84.5 | 3.6 | 0.6 |

These results indicate, not only that the compounds of formula (I) are less ulcerogenic than their parent acid, but that they have an anti-inflammatory and analgesic activity greater than the parent acid. In accordance with this data, 2-(3'-chloro-2'-methylanilino) 3-pyridine carboxylic derivatives of formula (I) are more analgesic than other derivatives described herein. Also, pivaloyloxymethyl ester of 2-(3'-trifluoromethylanilino)-3-pyridine carboxylic acid, act as anti-inflammatory agent more than as antinociceptive agents.

What is claimed:

1. A method of alleviating pain and inflammation in mammals, including humans, suffering from pain and inflammation, which comprises; administering to the mammal an effective amount of a compound selected from those of the formula:

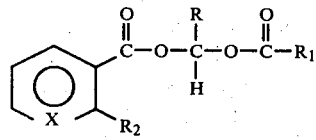

wherein X represents a moiety of formula:

$-N=$;

R taken independently is hydrogen; $R_1$ taken independently is isobutyl; and R and $R_1$ when taken together form the divalent moiety of formula:

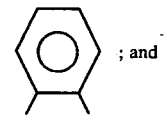 ; and $R_2$ is a group of formula:

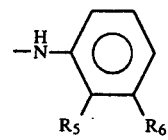

wherein when $R_1$ and R are taken together, then $R_5$ is methyl and $R_6$ is chlorine, and when $R_1$ is isobutyl and R is hydrogen, then $R_5$ is selected from the group consisting of hydrogen and methyl and $R_6$ is selected from the group consisting of chlorine and trifluoromethyl; and the pharmaceutically acceptable acid addition salts thereof.

2. The method of claim 1 wherein the compound selected is phthalidyl 2-[3'-chloro-2'-methyl anilino]-pyridine-3-carboxylate.

3. The method of claim 1 wherein the compound selected is pivaloyloxymethyl 2-[3'-(trifluoromethyl)anilino]-pyridine-3-carboxylate.

4. The method of claim 1 wherein the compound selected is pivaloyloxymethyl 2[(3'-chloro-2'-methyl)anilino]-pyridine-3-carboxylate.

* * * * *